(12) United States Patent
Sierra

(10) Patent No.: US 7,091,225 B2
(45) Date of Patent: Aug. 15, 2006

(54) SUBSTITUTED OXAZOLES AND THIAZOLES AS HPPAR ALPHA AGONISTS

(75) Inventor: Michael Lawrence Sierra, Les Ulis (FR)

(73) Assignee: SmithKline Beecham Corporation, Philadelphia, PA (US)

( * ) Notice: Subject to any disclaimer, the term of this patent is extended or adjusted under 35 U.S.C. 154(b) by 427 days.

(21) Appl. No.: 10/451,298

(22) PCT Filed: Dec. 18, 2001

(86) PCT No.: PCT/EP01/14886

§ 371 (c)(1),
(2), (4) Date: Nov. 17, 2003

(87) PCT Pub. No.: WO02/50047

PCT Pub. Date: Jun. 27, 2002

(65) Prior Publication Data

US 2004/0147571 A1   Jul. 29, 2004

Related U.S. Application Data

(60) Provisional application No. 60/257,070, filed on Dec. 20, 2000.

(51) Int. Cl.
| | |
|---|---|
| *A61K 31/426* | (2006.01) |
| *A61K 31/421* | (2006.01) |
| *C07D 277/20* | (2006.01) |
| *C07D 263/30* | (2006.01) |

(52) U.S. Cl. .............. 514/365; 548/203; 548/204; 548/235; 548/236; 514/374

(58) Field of Classification Search ............ 548/203, 548/204, 235, 236; 514/365, 374
See application file for complete search history.

(56) References Cited

U.S. PATENT DOCUMENTS

| | | | |
|---|---|---|---|
| 6,518,290 B1 * | 2/2003 | Sierra | ............... 514/365 |
| 6,706,717 B1 * | 3/2004 | Barrish et al. | ......... 514/254.02 |
| 6,710,063 B1 * | 3/2004 | Chao et al. | .............. 514/365 |
| 6,723,740 B1 * | 4/2004 | Chao et al. | .............. 514/365 |

FOREIGN PATENT DOCUMENTS

| | | |
|---|---|---|
| EP | 1 067 109 | 10/2001 |
| WO | 01/00603 | 4/2001 |
| WO | 01/40207 | 7/2001 |

* cited by examiner

Primary Examiner—Golam M. M. Shameem
(74) Attorney, Agent, or Firm—Jennifer L. Fox

(57) ABSTRACT

Compounds of formula (I) and pharmaceutically acceptable salts, solvates and hydrolysable esters thereof wherein X is O or S X1 is O or S; X is S or O; R1 and R2 are independently H, methyl, or halogen; R4 and R5 are independently H or C1-3 alkyl or R4 and R5 may, together with the carbon atom to which they are bonded, form a 3–5 membered cycloalkyl ring; R6 and R7 are independently H, C1-3 alkyl, or allyl; each R3 is independently halogen, C1-6 straight or branched alkyl, or CF3; and y is 0, 1, 2, 3, 4 or 5 act as hPPAR alpha agonists.

19 Claims, No Drawings

SUBSTITUTED OXAZOLES AND THIAZOLES AS HPPAR ALPHA AGONISTS

This application is filed pursuant to 35 U.S.C. § 371 as a United States National Phase Application of International Application No. PCT/EP01/14886 filed Dec. 18, 2001, which claims priority from 60/257,070 filed Dec. 20, 2000.

The present invention relates to certain novel compounds. In particular, the present invention relates to compounds that activate the alpha subtype of the human peroxisome proliferator activated receptor ("hPPAR alpha"). The present invention also relates to method for preparing the compounds, their use in medicine, pharmaceutical compositions containing them and methods for the prevention or treatment of PPAR mediated diseases or conditions.

Several independent risk factors have been associated with cardiovascular disease. These include hypertension, increased fibrinogen levels, high levels of triglycerides, elevated LDL cholesterol, elevated total cholesterol, and low levels of HDL cholesterol. HMG CoA reductase inhibitors ("statins") are useful for treating conditions characterized by high LDL-c levels. It has been shown that lowering LDL-c is not sufficient for reducing the risk of cardiovascular disease in some patients, particularly those with normal LDL-c levels. This population pool is identified by the independent risk factor of low HDL-c. The increased risk of cardiovascular disease associated with low HDL-c levels has not yet been successfully addressed by drug therapy (i.e., currently there are no drugs on the market that are useful for raising HDL-c >40%). (Bisgaier, C. L.; Pape, M. E. *Curr. Pharm. Des.* 1998, 4, 53–70).

Syndrome X (including metabolic syndrome) is loosely defined as a collection of abnormalities including hyperinsuinlemia, obesity, elevated levels of trigycerides, uric acid, fibrinogen, small dense LDL-c particles, and plasminogen activator inhibitor 1 (PAI-1), and decreased levels of HDL-c.

NIDDM is described as insulin resistance which in turn causes anomalous glucose output and a decrease in glucose uptake by skeletal muscle. These factors eventually lead to impaired glucose tolerance (IGT) and hyperinsulinemia.

Peroxisome Proliferator Activated Receptors (PPARs) are orphan receptors belonging to the steroid/retinoid receptor superfamily of ligand-activated transcription factors. See, for example, Willson, T. M. and Wahli, W., *Curr. Opin. Chem. Biol.*, (1997), Vol. 1, pp 235–241.

Three mammalian Peroxisome Proliferator-Activated Receptors have been isolated and termed PPAR-alpha, PPAR-gamma, and PPAR-delta (also known as NUC1 or PPAR-beta). These PPARs regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signaling cascade and lipid homeostasis (H. Keller and W. Wahli, *Trends Endoodn. Met* 291–296, 4 (1993)).

Certain compounds that activate or otherwise interact with one or more of the PPARs have been implicated in the regulation of triglyceride and cholesterol levels in animal models. See, for example, U.S. Pat. No. 5,847,008 (Doebber et al.) and U.S. Pat. No. 5,859,051 (Adams et al.) and PCT publications WO97/28149 (Leibowitz et al.) WO99/04815 (Shimokawa et al.), WO00/08002 (Collins et al), and WO99/46232 (Tajima et al).

Fibrates are a class of drugs which may lower serum triglycerides 20–50%, lower LDL-c 10–15%, shift the LDL particle size from the more atherogenic small dense to normal dense LDL-c, and increase HDL-c 10–15%. experimental evidence indicates that the effects of fibrates on serum lipids are mediated through activation of PPAR alpha. See, for example, B. Staels et al., *Curr. Pharm. Des.,* 1–14, 3 (1), (1997). Activation of PPAR alpha results in transcription of enzymes that increase fatty acid catabolism and decrease de-novo fatty acid synthesis in the liver resulting in decreased triglyceride synthesis and VLDL-c production/secretion. In addition, PPAR alpha activation decreases production of apoC-III. Reduction in apoC-III, an inhibitor of LPL activity, increases clearance of VLDL-c. See, for example, J. Auwerx et al., *Atherosclerosis*, (Shannon, Irel.), S29–S37, 124 (Suppl), (1996). PPAR alpha ligands may be useful for the treatment of dyslipidemia and cardiovascular disorders, see Fruchart, J. C., Duriez, P., and Staels, B., *Curr. Opin. Lipidol.* (1999), Vol 10, pp 245–257.

WO99/46232 (Ono Pharmaceutical Co Ltd) discloses carboxylic acid derivatives as PPAR regulators useful as for example hypoglycemic and lipid lowering agents.

The present inventors have found a subgroup of compounds disclosed in WO99/46232 are potent activators of PPAR subtype alpha.

According to a first aspect of the invention there is provided a compound of formula (I) and pharmaceutically acceptable salts, solvates and hydrolysable esters thereof:

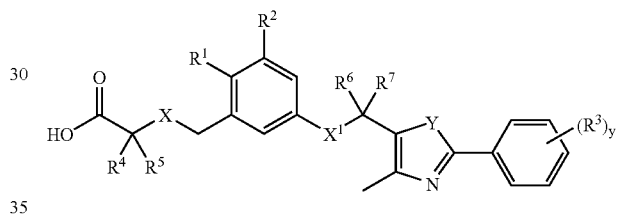

wherein
X is O or S;
$X^1$ is O or S;
Y is S or O;
$R^1$ and $R^2$ are independently H, methyl or halogen;
$R^4$ and $R^5$ are independently H or $C_{1-3}$ alkyl or $R^4$ and $R^5$ may, together with the carbon atom to which they are bonded, form a 3–5 membered cycloalkyl ring;
$R^6$ and $R^7$ are independently H, $C_{1-6}$ alkyl, allyl;
each $R^3$ is independently halogen, $C_{1-6}$ straight or branched alkyl, or $CF_3$; and
y is 0, 1, 2, 3, 4, or 5.

In another aspect, the present invention discloses a method for prevention or treatment of a disease or condition mediated by one or more human PPAR alpha, gamma or delta ("hPPARs") comprising administration of a therapeutically effective amount of a compound of this invention. hPPAR mediated diseases or conditions or conditions include dyslipidemia including associated diabetic dyslipidemia and mixed dyslipidemia, syndrome X (as defined in this application this embraces metabolic syndrome), heart failure, hypercholesteremia, cardiovascular disease including atherosclerosis, arteriosclerosis, and hypertriglyceridemia, type II diabetes mellitus, type I diabetes, insulin resistance, hyperlipidemia, inflammation, epithelial hyperproliferative diseases including eczema and psoriasis and conditions associated with the lung and gut and regulation of appetite and food intake in subjects suffering from disorders such as obesity, anorexia bulimia, and anorexia nervosa. In particular, the compounds of this invention are useful in the treatment and prevention of diabetes and cardiovascular diseases and conditions including atherosclerosis, arteriosclerosis, hypertriglyceridemia, and mixed dyslipidaemia.

In another aspect, the present invention provides pharmaceutical compositions comprising a compound of the invention, preferably in association with a pharmaceutically acceptable diluent or carrier.

In another aspect, the present invention provides a compound of the invention for use in therapy, and in particular, in human medicine.

In another aspect, the present invention provides the use of a compound of the invention for the manufacture of a medicament for the treatment of a hPPAR mediated disease or condition.

In another aspect, the present invention provides a method of treatment of a patent suffering from a hPPAR mediated disease or condition comprising the administration of a therapeutically effective amount of a compound of the invention.

As used herein, "a compound of the invention" means a compound of formula (I) or a pharmaceutically acceptable salt, solvate, or hydrolyzable ester thereof.

While hydrolyzable esters are included in the scope of this invention, the acids are preferred because the data suggests that while the esters are useful compounds, it may actually be the acids to which they hydrolyze that are the active compounds. Esters that hydrolyze readily can produce the carboxylic acid in the assay conditions or in vivo. Generally the carboxylic acid is active in both the binding and transient transfection assays, while the ester does not usually bind well but is active in the transient transfection assay presumably due to hydrolysis. Preferred hydrolysable esters are $C_{1-6}$ alkyl esters wherein the alkyl group may be straight chain or branched chain. Methyl or ethyl esters are more preferred.

Preferably X is O.
Preferably $X^1$ is O.
Preferably at least one of $R^1$ and $R^2$ is H. Most preferably, $R^1$ and $R^2$ are both H.
Preferably $R^6$ and $R^7$ are both H.
Preferably Y is S.
Preferably $R^4$ and $R^5$ both are $CH_3$ or both are hydrogen, with both $R^4$ and $R^5$ being $CH_3$ particularly preferred.
Preferably y is 1 or 2. When y is 2, preferably one of the substituents is halogen; more preferably one is halogen and the other is $CF_3$. Most preferably y is 1. When y is 1, preferably the substituent is in the para position on the ring and is more preferably $CF_3$.

While the preferred groups for each variable have generally been listed above separately for each variable, preferred compounds of this invention include those in which several or each variable in Formula (I) is selected from the preferred, more preferred, or most preferred groups for each variable. Therefore, this invention is intended to include all combinations of preferred, more preferred, and most preferred groups.

The hPPAR agonists of formula (I) may be agonists of only one type ("selective agonists"), agonists for two PPAR subtypes ("dual agonists"), or agonists for all three subtypes ("pan agonists"). As used herein, by "agonist", or "activating compound", or "activator", or the like, is meant those compounds which have a pKi of at least 6.0 preferably at least 7.0 to the relevant PPAR, for example hPPARalpha in the binding assay described below, and which achieve at least 50% activation of the relevant PPAR relative to the appropriate indicated positive control in the transfection assay described below at concentrations of $10^{-5}$ M or less. More preferably, the agonists of this invention achieve 50% activation of at least one human PPAR in the relevant transfection assay at concentrations of $10^{-6}$ M or less. Preferably, the compounds of formula (I) are hPPAR agonists. More preferably the compounds are hPPARalpha agonists.

Most preferably, the compounds of formula (I) are selective hPPARalpha agonists. As used herein, a "selective hPPAR alpha agonist" is a hPPARalpha agonist whose $EC_{50}$ for PPARalpha is at least 10 fold lower than its $EC_{50}$ for PPAR gamma and PPAR delta. Such selective compounds may be referred to as "10-fold selective." $EC_{50}$ is defined in the transfection assay described below and is the concentration at which a compound achieves 50% of its maximum activity. Most preferred compounds are greater than 100-fold selective hPPARalpha agonists (see Table 1).

TABLE 1

PPAR Transactivation activity for selected compounds.

| Example no. | human $_\alpha EC_{50}$ µM | human $_\delta EC_{50}$ µM | human $_\gamma EC_{50}$ µM |
|---|---|---|---|
| Example 2 | 0.002 | 3.200 | 2.600 |
| Example 4 | 0.010 | 1.600 | 3.600 |

Preferred compounds of the present invention include:
2-methyl-2-{(3-[4-methyl-2-(4-trifluoromethylphenyl)thiazol-5-yl]methoxy)benzyloxy}propionic acid ethyl ester;
2-methyl-2-{(3-[4-methyl-2-(4-trifluoromethylphenyl)thiazol-5-yl]methoxy)benzyloxy}propionic acid;
2-{[(3-[4-methyl-2-(4-trifluoromethylphenyl)thiazol-5-yl]methoxy)benzyl]thio}acetic acid methyl ester;
2-{[(3-[4-methyl-2-(4-trifluoromethylphenyl)thiazol-5-yl]methoxy)benzyl]thio}acetic acid;
2-{(3-[4-methyl-2-(4-trifluoromethylphenyl)thiazol-5-yl]methoxy)benzyloxy}acetic acid ethyl ester;
2-{(3-[4-methyl-2-(4-trifluoromethylphenyl)thiazol-5-yl]methoxy)benzyloxy}acetic acid;
2-methyl-2-[3-{1-[4-methyl-2-(4-trifluoromethylphenyl)thiazol-5-yl]ethoxy}benzyloxy]propionic acid ethyl ester;
2-methyl-2-[3-{1-[4-methyl-2-(4-trifluoromethylphenyl)thiazol-5-yl]ethoxy}benzyloxy]propionic acid;
2-methyl-2-[3-{1-methyl-1-[4-methyl-2-(4-trifluoromethylphenyl)thiazol-5-yl]ethoxy}benzyloxy]propionic acid ethyl ester;
2-methyl-2-[3-{1-methyl-1-[4-methyl-2-(4-trifluoromethylphenyl)thiazol-5-yl]ethoxy}benzyloxy]propionic acid;
2-methyl-2-[3-{1-[4-methyl-2-(4-trifluoromethylphenyl)thiazol-5-yl]propyloxy}benzyloxy]propionic acid ethyl ester;
2-methyl-2-[3-{1-[4-methyl-2-(4-trifluoromethylphenyl)thiazol-5-yl]propyloxy}benzyloxy]propionic acid;

Each of these preferred compounds is a hPPARalpha agonist.

A particularly preferred compound of the invention is:
2-methyl-2-{[(3-[4-methyl-2-(4-trifluoromethylphenyl)thiazol-5-yl]methoxy)phenyl]methoxy}propionic acid.

This particularly preferred compound is a selective hPPAR alpha agonist.

Those skilled in the art will recognize that stereocenters exist in compounds of formula (I). Accordingly, the present invention includes all possible stereoisomers and geometric isomers of formula (I) and includes not only racemic compounds but this invention is also intended to cover each of these isomers in their racemic, enriched, or purified forms. When a compound of formula (I) is desired as a single enantiomer, it may be obtained either by resolution of the final product or by stereospecific synthesis using an optically active catalyst or a catalytic system with optically active ligands or isomerically pure starting material or any convenient intermediate. Resolution of the final product, an intermediate or a starting material may be effected by any suitable method known in the art. See, for example, *Stereochemistry of Carbon Compounds* by E. L. Eliel (Mcgraw Hill, 1962) and *Tables of Resolving Agents* by S. H. Wilen. Additionally, in situations where tautomers of the compounds of formula (I) are possible, the present invention is intended to include all tautomeric forms of the compounds. In particular, in many of the preferred compounds of this invention the carbon atom to which $R^6$ and $R^7$ are bonded is chiral. In some of these chiral compounds the activities at the various PPAR receptors varies between the S and R isomers. Which of these isomers is preferred depends on the particular desired utility of the compound. In other words, even with the same compound, it is possible that the S isomer will be preferred for some uses, while the R isomer will be preferred for others.

It will also be appreciated by those skilled in the art that the compounds of the present invention may also be utilized in the form of a pharmaceutically acceptable salt or solvate thereof. The physiologically acceptable salts of the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. Those skilled in the art of organic chemistry will appreciate that many organic compounds can form complexes with solvents in which they are reacted or from which they are precipitated or crystallized. These complexes are known as "solvents". For example, a complex with water is known as a "hydrate". References hereinafter to a compound according to the invention include both compounds of formula (I) and their pharmaceutically acceptable salts and solvates.

The compounds of the invention and their pharmaceutically acceptable derivatives are conveniently administered in the form of pharmaceutical compositions. Such compositions may conveniently be presented for use in conventional manner in admixture with one or more physiologically acceptable carriers or excipients.

While it is possible that compounds of the present invention may be therapeutically administered as the raw chemical, it is preferable to present the active ingredient as a pharmaceutical formulation. The carrier(s) must be "acceptable" in the sense of being compatible with the other ingredients of the formulation and not deleterious to the recipient thereof.

Accordingly, the present invention further provides for a pharmaceutical formulation comprising a compound of formula (I) or a pharmaceutically acceptable salt or solvate thereof together with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate orsorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 1–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, statins and/or other lipid lowering drugs for example MTP inhibitors and LDLR upregulators. The compounds of the invention may also be used in combination with antidiabetic agents, e.g. metformin, sulfonylureas and/or PPAR agonists (for example PPAR gamma agonists, including thiazolidinediones such as e.g. Pioglitazone and Rosiglitazone) or PPAR alpha/gamma agonists, or PPAR delta agonists wherein the PPAR delta agonists may be selective agonists for PPAR delta, have agonist activity at PPAR alpha or gamma (dual agonists) or activity at PPAR alpha and gamma (Pan agonists). The compounds may also be used in combination with antihypertensive agents such as calcium channel antagonists and ACE inhibitors. The invention thus provides in a further aspect the use of a combination comprising a compound of formula (I) with a further therapeutic agent in the treatment of a hPPAR mediated disease.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (I) is used in combination with a second therapeutic agent active against the same hPPAR mediated disease, the dose of each compound may differ from that when the compound is used alone. Appropriate doses will be readily appreciated by those skilled in the art.

Compounds of this invention may be conveniently prepared by a general process wherein a moiety like A is coupled to an alcohol (B or D) using the Mitsunobu protocol (O. Mitsunobu, 1981 Synthesis, p 1) or by alkylation of A using a

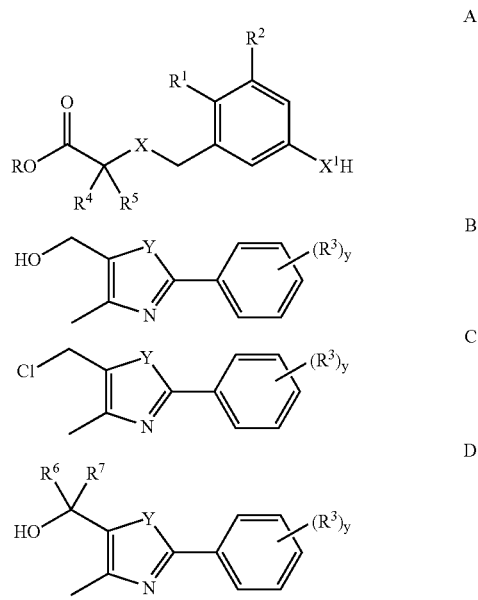

-continued

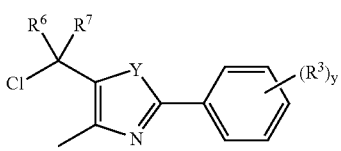

suitable non nucleophilic base such as $K_2CO_3$, $Cs_2CO_3$ or NaH, with an alkyl halide (C and E). Note that this synthesis is preferably carried out with the acid group protected by R although R may represent H. Preferably, R is 1–6 alkyl (straight chain or branched chain) which can be hydrolyzed off to give an acid of Formula (I), or if readily hydrolyzable, the resulting ester can be administered.

The intermediates of type (A) can be readily synthesized as outlined below. The synthesis of intermediates of type (B-E) are also illustrated below.

For example, when Y is S, X and $X^1$ are O, $R^1$ and $R^2$ are H, $R^4$ and $R^5$ are $CH_3$, y is 1 and $R^3$ is para-$CF_3$:

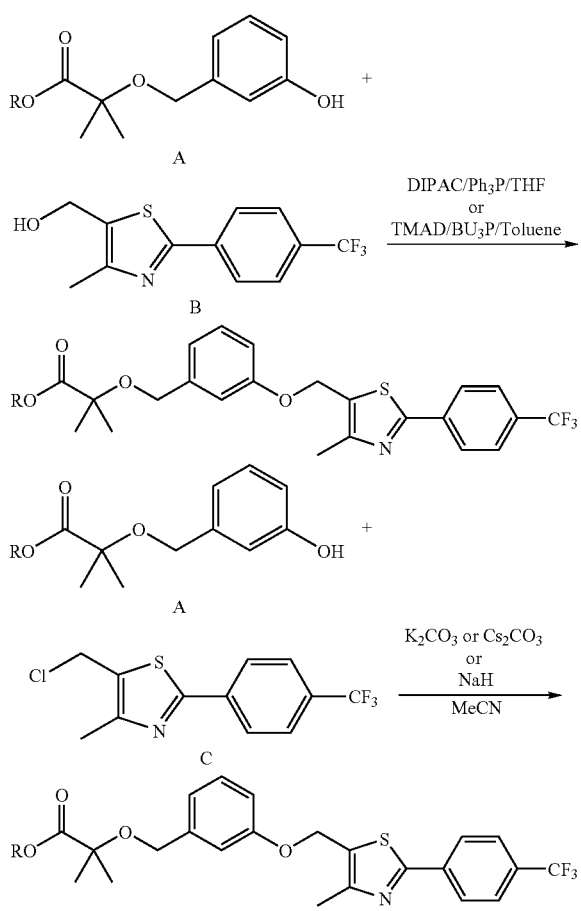

The invention is further illustrated by the following Intermediates and Examples which should not be construed as constituting a limitation thereto. The structures of the compounds were confirmed either by nuclear magnetic resonance (NMR) or mass spectrometry (MS). 1H NMR spectra were recorded on a Brucker 300 MHz spectrometer at ambient temperature. NMR shifts (δ) are given in parts per million (ppm), "mp" is melting point and is given in °C. Column chromatography was carried out using the technique described by W. C. Still et al, J. Org. Chem. 1978, 43, 2923–2925 on Merck silica gel 60 (40–63 μM).

Compounds used as starting materials are either commercially available compounds or known compounds.

Abbreviations:
tlc: thin layer chromatography
DMSO-$d_6$: deutorated dimethylsulfoxide
$CDCl_3$: deutorated chloroform
DMF: N,N-dimethylformamide
$Et_2O$: diethylether
EtOAc: Ethylacetate
MeOH: Methanol
EtOH: Ethanol
PBu3: Tributylphosphine
TMAD: Azodicarboxylic acid bis[dimethylamide]
THF: tetrahydrofuran
MEMCl: 2-methoxyethoxymethyl chloride
min: minutes
br: broad
s: singlet
d: doublet
dd: doublet of doublet
t: triplet
q: quartet
m: multiplet Intermediate 1:

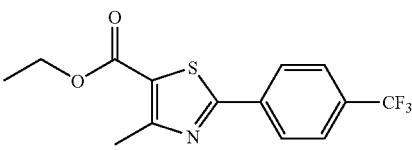

A solution of ethyl 2-chloroacetoacetate (35.3 g, 29.7 mL, 0.21 mol) and 4-(trifluoromethyl)thiobenzamide (44 g, 0.21 mol) in EtOH (300 mL) was refluxed overnight. After cooling to room temperature the solvent was removed in vacuo. The final product (intermediate 1) was recrystallized from a minimum of MeOH to afford 40 g (59%) of final product as a white solid.

$^1$H NMR ($CDCl_3$): δ 8.10 (d, 2H), 7.70 (d, 2H), 4.40 (q, 2H), 2.80 (s, 3H), 1.4 (t, 3H).

Intermediate 2:

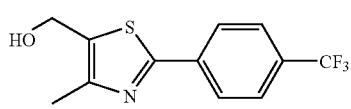

To a solution of intermediate 1 (1 mmol) in THF (100 mL) at 0° C. was added dropwise $LiAlH_4$ (1 equiv.). After the addition was complete, the reaction was stirred at 0° C. for 30 min then allowed to warm to room temperature and stirring continued overnight. The reaction was slowly hydrolyzed with ice cold $H_2O$ and the mixture extracted with $CH_2Cl_2$ (3×100 mL). The combined organic phase was dried over $Na_2SO_4$, filtered and evaporated under reduced pressure to afford the title compound as an off-white solid (83%).

$^1$H NMR ($CDCl_3$): δ 7.9 (d, 2H), 7.60 (d, 2H), 4.75 (s, 3H), 2.50 (bs, 1H), 2.35 (s, 3H).

Intermediate 3:

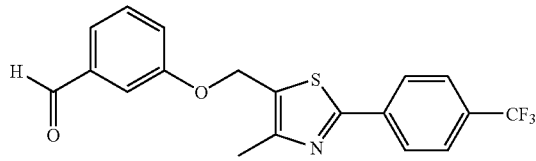

To intermediate 2 (1 mmol) in ThF (100 mL) at room temperature was added 3-hydroxybenzaldehyde (1.2 equiv., Aldrich), diisopropyl azodicarboxylate (1.5 equiv., Aldrich) and Ph$_3$P (1.5 equiv.). After the reaction was stirred for 18 h at room temperature, it was evaporated to dryness. The residue treated with 1N NaOH/H$_2$O and extracted with Et$_2$O (3×100 mL). The combined organic phase was dried over Na$_2$SO$_4$, filtered and evaporated under reduced pressure. The residue chromatographed eluting with CH$_2$Cl$_2$ (100%) to afford the title compound as an off-white solid (48%).

$^1$H NMR (CDCl$_3$): δ 10.05 (s, 1H), 8.05 (d, 2H), 7.75 (d, 2H), 7.55 (m, 3H), 7.35 (m, 1H), 5.35 (s, 2H), 2.60 (s, 3H).

Intermediate 4:

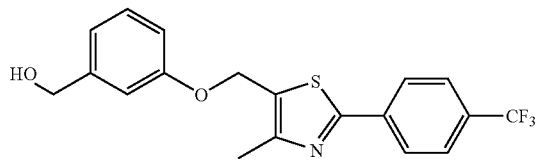

To intermediate 3 (1 mmol) in MeOH/THF (1:1) at room temperature was added NaBH$_4$ (1.2 equiv.) and the reaction was stirred for 18 h. The reaction was evaporated to dryness, treated with 1N HCl/H$_2$O and extracted with CH$_2$Cl$_2$ (3×100 mL). The combined organic phase was dried over Na$_2$SO$_4$, filtered and evaporated under reduced pressure to afford the title compound as a pale yellow solid (89%).

MS m/z 380 (M+1); 378 (M−1)

Intermediate 5:

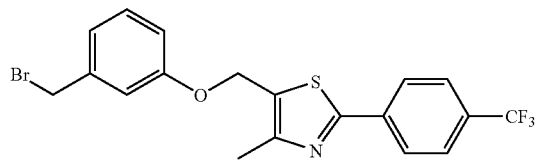

To intermediate 4 (1 mmol) in CH$_2$Cl$_2$ (30 mL) at room temperature was added PBr$_3$ (0.3 equiv.) and the reaction was stirred for 2 h. The reaction treated H$_2$O and extracted with CH$_2$Cl$_2$ (3×100 mL). The combined organic phase was dried over Na$_2$SO$_4$, filtered and evaporated under reduced pressure to afford the title compound as a pale yellow oil (83%).

$^1$H NMR (CDCl$_3$): δ 7.95 (d, 2H), 7.61 (d, 2H), 7.23 (d, 1H), 6.96 (m, 2H), 6.85 (m, 1H), 5.14 (s, 2H), 4.40 (s, 2H), 2.46 (s, 3H).

Intermediate 6:

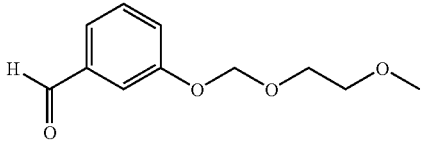

To 3-hydroxybenzaldehyde (1 mmol, Aldrich) in CH$_2$Cl$_2$ (100 mL) was added diisopropylethylamine (3 equiv.) followed dropwise by MEMCl (2 equiv.) and the reaction stirred 18 h at room temperature. The reaction was evaporated to dryness, treated with H$_2$O and extracted with EtOAc (3×100 mL). The combined organic phase was washed with 2×2M HCl, 2× sat. NaHCO$_3$ soln, H$_2$O and Brine. The organic phase was then dried over Na$_2$SO$_4$, filtered and evaporated under reduced pressure to afford the title compound as a pale brown oil (95%).

$^1$H NMR (CDCl$_3$): δ 9.95 (s, 1H), 7.55–7.25 (m, 4H), 5.30 (s, 2H), 3.80 (m, 2H), 3.50 (m, 2H), 3.35 (s, 3H)

Intermediate 7:

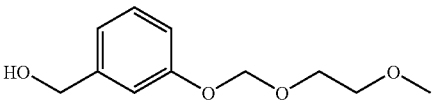

To intermediate 6 (1 mmol) in THF (50 mL) was added dropwise LiAlH$_4$ (1.3 equiv.) and the reaction was stirred at reflux for 2 h. The reaction was quenched with a sat. Na$_2$SO$_4$ soln. vaporated to dryness, treated with 1N HCl/H$_2$O and extracted with CH$_2$Cl$_2$ (3×100 mL). H$_2$O (60 mL) was added along with Et$_2$O (100 mL). The mixture was filterd through celite and the organic phase collected washed with brine, dried over Na$_2$SO$_4$, filtered and evaporated under reduced pressure to afford the title compound as a clear oil (88%).

$^1$H NMR (CDCl$_3$): δ 7.30–6.95 (m, 4H), 5.30 (s, 2H), 4.70 (d, 2H), 3.80 (m, 2H), 3.50 (m, 2H), 3.35 (s, 3H), 1.95 (t, 1H)

Intermediate 8:

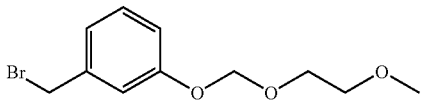

Dimethylsulfide (1.8 equiv.) was added dropwise to a suspension of NBS (1.5 equiv.) in CH$_2$Cl$_2$ (85 mL) at 0° C. The solution was cooled to −20° C. and intermediate 7 (1 mmol) in CH$_2$Cl$_2$ (8 mL) was added dropwise over 5 min. The reaction was stirred at 0° C. for 2 h then poured onto ice water, extracted with toluene (3×100 mL) and the organic phases combined. The combined organic phase was dried over MgSO$_4$, filtered and evaporated under reduced pressure to afford the title compound as a pale brown oil (50%).

$^1$H NMR (CDCl$_3$): δ 7.30–6.95 (m, 4H), 5.30 (s, 2H), 4.50 (d, 2H), 3.80 (m, 2H), 3.50 (m, 2H), 3.35 (s, 3H)

Intermediate 9:

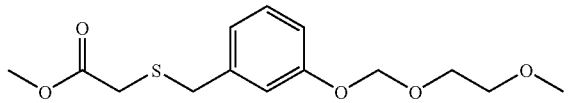

Methyl thioglycolate (1.4 equiv.) was dissolved in THF (95 mL), cooled to 0° C. and Et$_3$N (1.4 equiv.) added. Intermediate 8 (1 mmol) in THF (10 mL) was then added slowly. After the addition was complete, the reaction was allowed to warm to room temperature and stirred for 18 h. The reaction was then diluted with Et$_2$O (100 mL) and washed with: 1M HCl, then sat NaHCO$_3$ soln, then brine and dried over MgSO$_4$. The solution was filtered and evaporated under reduced pressure to afford the title compound as a pale brown oil (96%).

$^1$H NMR (CDCl$_3$): δ 7.30–6.95 (m, 4H), 5.30 (s, 2H), 3.90 (m, 4H), 3.70 (s, 2H), 3.50 (m, 2H), 3.35 (s, 3H), 3.10 (s, 3H)

Intermediate 10:

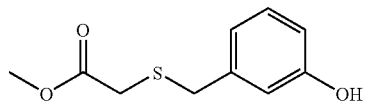

To intermediate 9 (1 mmol) was added a solution of acetyl chloride (3.7 equiv.) in MeOH (6 mL) at 0° C. The reaction was stirred for 18 h, then evaporated to dryness and azeotroped 2× absolute alcohol to afford the title compound as a pale brown oil (97%).

$^1$H NMR (CDCl$_3$): δ 7.20–6.70 (m, 4H), 5.10 (bs, 1H), 3.80 (s, 2H), 3.70 (s, 3H), 3.10 (s, 2H)

Intermediate 11:

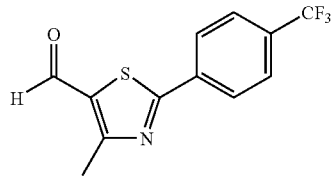

To a solution of Intermediate 2 (75.5 g, 0.276 mmol, 1 equiv.) in CH$_2$Cl$_2$ was added pyridinium chlorochromate (119 g, 0.552 mmol, 2eq). Then the resulting mixture was stirred at room temperature for 3 hours. The mixture was decanted one night and then filtered over celite and evaporated off. The residue was purified by flash chromatography using CH$_2$Cl$_2$ as eluent to give the title compound as a yellow solid (71 g, 0.26 mmol) in a 61.5% yield.

GC/MS: C$_{12}$H$_8$F$_3$NOS: m/z 271

Intermediate 12:

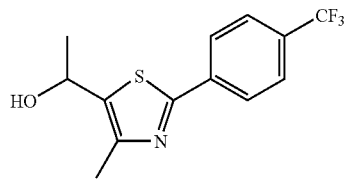

To a solution of intermediate 11 (1.9 g, 7 mmol) in 25 mL of THF was added slowly at −10° C., a solution of 1.4M methylmagnesium bromide in THF (7 mL, 11.9 mmol, 1.4 equiv.). The mixture was naturally warmed at room temperature and then stirred for 1.5 hour. The resulting mixture was quenched with saturated NH$_4$Cl solution (100 mL) and extracted with EtOAc (2×250 mL). The organic phase was washed with brine and water, and then dried over Na$_2$SO$_4$ and evaporated off to give the title compound as a yellow solid (1.9 g, 6.96 mmol) in a 99% crude yield.

GC/MS: C$_{13}$H$_{12}$F$_3$NOS: m/z 287

MP: 147° C.

Intermediate 13:

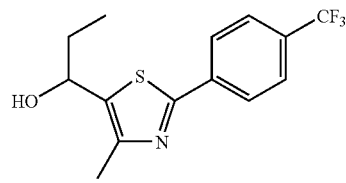

To a solution of intermediate 11 (4.05 g, 15 mmol) in 50 mL of THF was added slowly at −10° C., a solution of 3M ethylmagnesium bromide in Et$_2$O (5.5 mL, 16.5 mmol, 1.1 equiv.). The mixture was naturally warmed at room temperature and then stirred for 1.5 hour. The resulting mixture was quenched with saturated NH$_4$Cl solution (100 mL) and extracted with EtOAc (3×100 mL). The organic phase was washed with brine and water, and then dried over Na$_2$SO$_4$ and evaporated off. The residue was taken up with a mixture of isopropyl ether and petroleum ether. The white solid obtained was filtered to give the title compound (4.31 g, 14.3 mmol) in a 95% yield.

GC/MS: C$_{14}$H$_{14}$F$_3$NOS: m/z 301

MP: 104–106° C.

Intermediate 14:

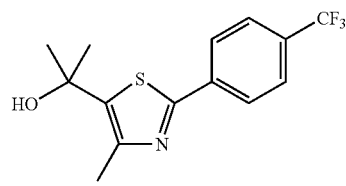

To a solution of intermediate 1 (3 g, 9.5 mmol) in 50 mL of THF was added slowly at −10° C., a solution of 1.4M methylmagnesium bromide in THF (20.4 mL, 3 equiv.). The mixture was naturally warmed at room temperature and then stirred for 1.5 hour. Another 2 eq. of 1.4M methylmagnesium bromide in THF (13.6 mL, 2 equiv.) was added and the reaction stirred for 2 h at room temperature. The resulting mixture was quenched with saturated NH$_4$Cl solution (100 mL) and extracted with Et$_2$O (3×100 mL). The organic phase was washed with brine and water, and then dried over Na$_2$SO$_4$ and evaporated off. The residue was chromatographed with CH$_2$Cl$_2$(100%) followed by a mixture of CH$_2$Cl$_2$/MeOH (99/1) to afford the title compound (2.35 g, 7.8 mmol) as a beige solid in 82% yield.

GC/MS: C$_{14}$H$_{14}$F$_3$NOS: m/z 301 $^1$H NMR (CDCl$_3$): δ 7.90 (d, 2H), 7.60 (d, 2H), 2.55 (s, 3H), 1.70 (s, 6H)

Intermediate 15:

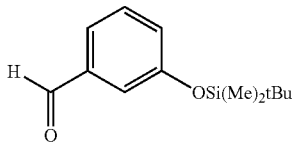

To 3-hydroxybenzaldehyde (10 g, 81.9 mmol, Aldrich) in CH$_2$Cl$_2$ was added NEt$_3$ (17.1 mL, 0.12 mol, 1.5 equiv.), tBuMe$_2$SiCl (14.8 g, 98.2 mmol, 1.2 equiv.) and the reaction stirred at room temperature while it was followed by t.l.c. (silica gel, CH$_2$Cl$_2$ 100%; Rf=0.9). The reaction was treated with H$_2$O and extracted with CH$_2$Cl$_2$ (3×100 mL). The organic layers combined, dried over Na$_2$SO$_4$, filtered and the solvent evaporated to afford a yellow oil. The oil was taken up in CH$_2$Cl$_2$ and passed through a silica gel plug to remove the polar impurities. The solvent was removed under vacuum to afford the title compound (18.8 g, 79.2 mmol, 97%) as a clear yellow liquid.

$^1$H NMR (CDCl$_3$): δ 9.73 (s, 1H), 7.25 (m, 1H), 7.15 (t, 1H), 7.05 (m, 1H), 6.85 (m, 1H), 0.75 (s, 9H), 0.0 (s, 6H)

Intermediate 16:

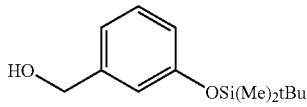

To intermediate 15 (10 g, 42 mmol) in THF (200 mL) was added NaBH$_4$ (2.06 g, 54.5 mmol, 1.2 equiv.) and the reaction stirred at room temperature while it was followed by t.l.c. (silica gel, cyclohexane/EtOAc: 5/5; Rf=0.75). The reaction was hydrolyzed slowly with cold H$_2$O/1N HCl and extracted with CH$_2$Cl$_2$ (3×200 mL). The organic layers combined, dried over Na$_2$SO$_4$, filtered and the solvent evaporated to afford a yellow oil. The oil was taken up in CH$_2$Cl$_2$ and passed through a silica gel plug to remove the polar impurities. The solvent was removed under vacuum to afford the title compound (8.8 g, 36.8 mmol, 87%) as a clear pale-yellow solid.

$^1$H NMR (CDCl$_3$): δ 7.00 (t, 1H), 6.75 (d, 1H), 6.65 (bs, 1H), 6.55 (m, 1H), 4.40 (s, 2H), 1.65 (bs, 1H), 0.75 (s, 9H), 0.0 (s, 6H)

Intermediate 17:

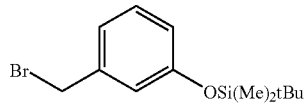

To intermediate 16 (5 g, 20.9 mmol) in THF (125 mL) was added the PPh$_3$ (8.84 g, 33.7 mmol, 1.5 equiv.), CBr$_4$ (8.20 g, 24.7 mmol, 1.1 equiv.) and the reaction stirred at room temperature while it was followed by t.l.c. (silica gel, cyclohexane/EtOAc: 5/5; Rf=0.95). The reaction was filtered through celite to remove the precipitate and the solvent removed under vacuum. The residue was taken up in cyclohexane and passed through a silica gel plug to remove the polar impurities. The solvent was removed under vacuum to afford the title compound (6.29 g, 20.9 mmol, 100%) as a clear pale-yellow solid.

$^1$H NMR (CDCl$_3$): δ 6.95 (t, 1H), 6.75 (d, 1H), 6.65 (bs, 1H), 6.55 (m, 1H), 4.20 (s, 2H), 0.75 (s, 9H), 0.0 (s, 6H)

Intermediate 18:

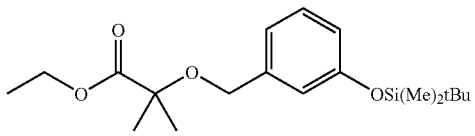

To ethyl 2-hydroxyisobutyrate (5.46 mL, 39.9 mmol, Aldrich) in THF (50 mL) was added NaH (1.6 g, 39.9 mmol) and the reaction stirred for 15 min. Intermediate 17 (5 g, 16.6 mmol, 0.4 equiv.) was added and the reaction heated to reflux with stirring while it was followed by t.l.c. (silica gel, CH$_2$Cl$_2$ 100%; Rf=0.75). The reaction was cooled to room temperature, evaporated to dryness, treated with H$_2$O and extracted with EtOAc (3×50 mL). The combined organic phase was dried over Na$_2$SO$_4$, filtered and evaporated under reduced pressure. The dark red oil was chromatographed eluting with CH$_2$Cl$_2$ (100%) to afford the title compound as a clear oil (2.1 g, 6.0 mmol, 36%).

GC/MS: C$_{19}$H$_{32}$O$_4$Si: m/z 352

$^1$H NMR (CDCl$_3$): δ 6.95 (t, 1H), 6.75 (d, 1H), 6.65 (bs, 1H), 6.55 (m, 1H), 4.20 (s, 2H), 4.00 (q, 2H), 1.3 (s, 6H), 1.10 (t, 3H), 0.80 (s, 9H), 0.0 (s, 6H).

Intermediate 19:

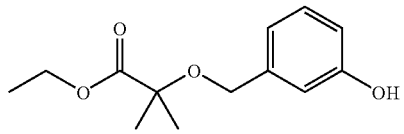

To intermediate 18 (2.1 g, 6.0 mmol) in CH$_2$Cl$_2$ (75 mL) was added 1M Bu$_4$NF in THF (11.9 mL, 12 mmol, 2 equiv.) and the reaction was stirred at room temperature while it was followed by t.l.c. (silica gel, CH$_2$Cl$_2$: 100%; Rf=0.2). The reaction was treated with H$_2$O/1N HCl and extracted with CH$_2$Cl$_2$ (3×50 mL). The combined organic phase was dried over Na$_2$SO$_4$, filtered and evaporated under reduced pressure. The yellow oil was taken up in CH$_2$Cl$_2$ (200 mL) and passed through a silica gel plug. EtOAc (75 mL) was used to recover the desired compound. The solvent was removed under vacuum to afford the title compound (1.34 g, 5.6 mmol, 94%) as a clear yellow liquid.

$^1$H NMR (CDCl$_3$): δ 7.05 (t, 1H), 6.80 (m, 2H), 6.60 (m, 1H), 4.30 (s, 2H), 4.10 (q, 2H), 1.40 (s, 6H), 1.20 (t, 3H)

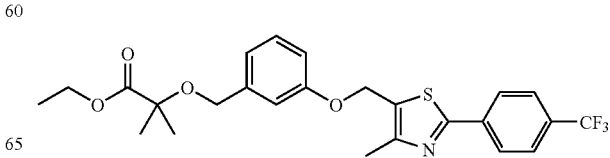

EXAMPLE 1

2-methyl-2-{(3-[4-methyl-2-(4-trifluoromethylphenyl)thiazol-5-yl]methoxy)benzyloxy}propionic acid ethyl ester To ethyl 2-hydroxyisobutyrate (1.25 equiv., Avocado) in THF (20 mL) was added NaH (1.25 equiv.) and the reaction stirred for 15 min. Intermediate 5 (1 mmol) was added and the reaction stirred at reflux for 18 h. The reaction was evaporated to dryness, treated with H$_2$O and extracted with CH$_2$Cl$_2$ (3×100 mL). The combined organic phase was dried over Na$_2$SO$_4$, filtered and evaporated under reduced pressure. The residue was chromatographed eluting with CH$_2$Cl$_2$/MeOH (98:2) to afford the title compound as a clear oil (31%).

$^1$H NMR (CDCl$_3$): δ 7.95 (d, 2H), 7.65 (d, 2H), 7.20 (t, 1H), 7.00 (bs, 1H), 6.95 (m, 1H), 6.80 (m, 1H), 5.15 (s, 2H), 4.40 (s, 2H), 4.15 (q, 2H), 2.45 (s, 3H), 1.45 (s, 6H), 1.25 (t, 3H)

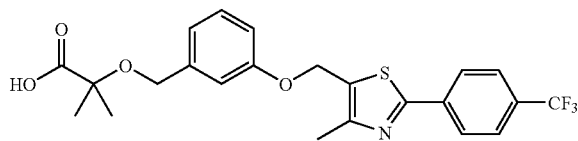

EXAMPLE 2

2-methyl-2-{(3-[4-methyl-2-(4-trifluoromethylphenyl)thiazol-5-yl]methoxy)benzyloxy}propionic acid To example 1 (1 mmol) in EtOH (100 mL) was added 1N NaOH (1.5 equiv.) and the reaction heated to 80° C. After 2 h, the reaction was evaporated to dryness, treated with 1N HCl (1.5 equiv.) and extracted with CH$_2$Cl$_2$ (3×100 mL). The combined organic phase was dried over Na$_2$SO$_4$, filtered and evaporated under reduced pressure. The residue was taken up in pentane to afford the title compound as a white solid (25%).

$^1$H NMR (CDCl$_3$): δ 7.95 (d, 2H), 7.65 (d, 2H), 7.25 (t, 1H), 6.95 (m, 3H), 5.20 (s, 2H), 4.50 (s, 2H), 2.50 (s, 3H), 1.50 (s, 6H); Mp 116–117° C.

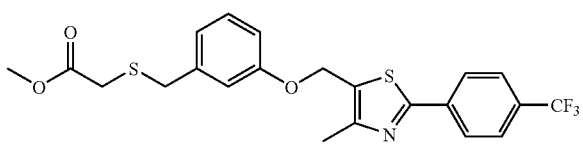

EXAMPLE 3

2-{[(3-[4methyl-2-(4-trifluoromethylphenyl)thiazol-5-yl]methoxy)benzyl]thio}acetic acid methyl ester To intermediate 2 (1 mmol) in THF (5 mL) was added intermediate 10 (1 mmol), Bu$_3$P (1.1 equiv.), morpholide (1.1 equiv.) and the reaction stirred for 48 h at room temperature. The reaction was evaporated to dryness, treated with H$_2$O and extracted with CHCl$_3$ (3×100 mL). The combined organic phase was dried over Na$_2$SO$_4$, filtered and evaporated under reduced pressure. The residue was chromatographed eluting with cyclohexane/EtOAc (gradient: 10:1 to 3:1) to afford the title compound as a clear oil (56%).

$^1$H NMR (CDCl$_3$): δ 8.00 (d, 2H), 7.65 (d, 2H), 7.25 (t, 1H), 7.00 (m, 2H), 6.85 (m, 1H), 5.20 (s, 2H), 4.80 (s, 2H), 3.70 (s, 3H), 3.10 (s, 2H), 2.70 (s, 3H)

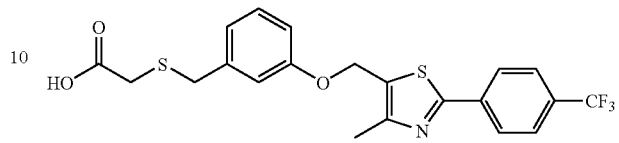

EXAMPLE 4

2-{[(3-[4-methyl-2-(4-trifluoromethylphenyl)thiazol-5-yl]methoxy)benzyl]thio}acetic acid To example 3 (1 mmol) in THF (10 mL) was added 2N NaOH (1.5 equiv.) and the reaction heated to 60° C. After 1.5 h, the reaction was evaporated to dryness, treated with 1N HCl (1.5 equiv.) and extracted with CHCl$_3$ (3×20 mL). The combined organic phase was dried over Na$_2$SO$_4$, filtered and evaporated under reduced pressure to afford the title compound as a clear oil (54%).

$^1$H NMR (CDCl$_3$): δ 8.00 (d, 2H), 7.65 (d, 2H), 7.25 (t, 1H), 6.95 (m, 2H), 6.90 (m, 1H), 5.20 (s, 2H), 4.80 (s, 2H), 3.10 (s, 2H), 2.50 (s, 3H); LC/UV (250 nm) 3.5 min

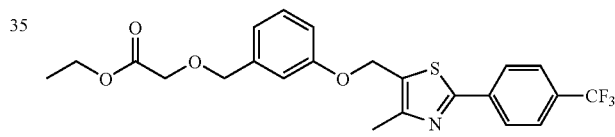

EXAMPLE 5

2-{(3-[4-methyl-2-(4-trifluoromethylphenyl)thiazol-5-yl]methoxy)benzyloxy}acetic acid ethyl ester To ethyl glycolate (2 mL, 17.8 mmol) in THF (20 mL) was added NaH (711 mg, 17.8 mmol, 1 equiv.) and the reaction stirred for 15 min. The reaction was evaporated to dryness, rinsed with pentane and re-evaporated to dryness (Note: the ethyl glycolate sodium salt is hydroscopic). To intermediate 5 (320 mg, 0.72 mmol, 0.04 equiv.) was added the ethyl glycolate sodium salt and the reaction stirred at room temperature for 1 h. The reaction was evaporated to dryness, treated with H$_2$O and extracted with CH$_2$Cl$_2$ (3×100 mL). The combined organic phase was washed with brine, dried over Na$_2$SO$_4$, filtered and evaporated under reduced pressure. The residue was chromatographed eluting with CH$_2$Cl$_2$ (100%) to afford the title compound as a clear oil (24%).

MS m/z 466 (M+1); m/z 465 (M−1)

$^1$H NMR (CDCl$_3$): δ 7.95 (d, 2H), 7.60 (d, 2H), 7.20 (t, 1H), 6.95 (bs, 1H), 6.90 (m, 1H), 6.80 (m, 1H), 5.10 (s, 2H), 4.55 (s, 2H), 4.15 (q, 2H), 4.05 (s, 2H), 2.45 (s, 3H), 1.20 (t, 3H)

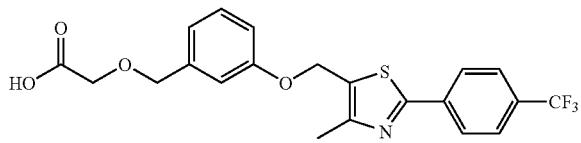

EXAMPLE 6

2-{(3-[4-methyl-2-(4-trifluoromethylphenyl)thiazol-5-yl]methoxy)benzyloxy}acetic acid To example 5 (1 mmol) in EtOH (100 mL) was added 1N LiOH.H$_2$O (2 equiv.) and the reaction heated to 40° C. After 3 h, the reaction was evaporated to dryness, treated with 1N HCl (1.5 equiv.) and extracted with CH$_2$Cl$_2$ (3×100 mL). The combined organic phase was dried over Na$_2$SO$_4$, filtered and evaporated under reduced pressure. The residue was taken up in cyclohexane to afford the title compound as a white solid (100%).

MS m/z 438 (M+1)

$^1$H NMR (CDCl$_3$): δ 8.20 (d, 2H), 7.85 (d, 2H), 7.45 (t, 1H), 6.10 (m, 3H), 5.35 (s, 2H), 4.75 (s, 2H), 4.25 (s, 2H), 2.7 (s, 3H); Mp 121° C.

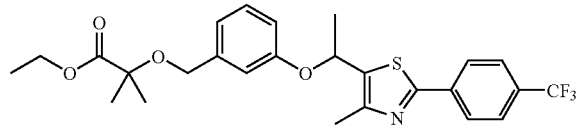

EXAMPLE 7

2-methyl-2-[3-{1-[4-methyl-2-(4-trifluoromethylphenyl)tiazol-5-yl]ethoxy}benzyloxy]propionic acid ethyl ester TMAD (315 mg, 1.8 mmol, 1.5 equiv., Fluka) and PBu$_3$ (452 μL, 1.8 mmol, 1.5 equiv., Fluka) in THF (50 mL) were stirred at room temperature until the solution became uncolored. To the solution was added intermediate 19 (290 mg, 1.2 mmol, 1 equiv.) followed by intermediate 12 (350mg, 1.2 mmol) and the reaction stirred at room temperature for 18 h. The reaction was evaporated to dryness and chromatographed eluting with CH$_2$Cl$_2$/cyclohexane (85:15) to afford the title compound as a brown oil (170 mg, 0.33 mmol, 28%).

MS m/z 506 (M−1)

$^1$H NMR (CDCl$_3$): δ 7.75 (d, 2H), 7.45 (d, 2H), 6.95 (t, 1H), 6.80 (bs, 1H), 6.75 (d, 1H), 6.60 (m, 1H), 5.45 (q, 1H), 4.25 (s, 2H), 4.05 (q, 2H), 2.30 (s, 3H), 1.30 (s, 3H), 1.25 (s, 3H), 1.05 (t, 3H)

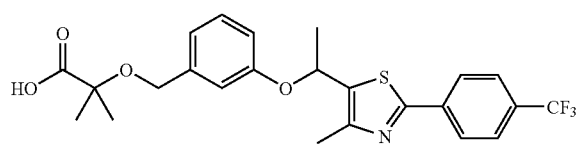

EXAMPLE 8

2-methyl-2-[3-{1-[4methyl-2-(4-trifluoromethylphenyl)thiazol-5-yl]ethoxy}benzyloxy]propionic acid To example 7 (170 mg, 0.33 mmol) in EtOH (25 mL) was added 1N NaOH (500 μL, 0.50 mmol, 1.5 equiv.) and the reaction heated to 50° C. with stirring for 18 h. Another 2.5 equiv. of 1N NaOH (830 μL, 0.83 mmol) was added and the reaction stirred for 4 h at 50° C. The reaction was evaporated to dryness, neutralized with 1N HCl and extracted with CH$_2$Cl$_2$ (3×50 mL). The combined organic phase was washed with water, dried over Na$_2$SO$_4$, filtered and evaporated to dryness. The residue was chromatograghed eluting with CH$_2$Cl$_2$/MeOH (gradient: 98:2 to 90:10) to afford the title compound (110 mg, 0.23 mmol, 69%) as a viscous white oil.

MS m/z 478 (M−1)

$^1$H NMR (CDCl$_3$): δ 7.85 (d, 2H), 7.45 (d, 2H), 7.15 (t, 1H), 6.90 (bs, 1H), 6.85 (d, 1H), 6.75 (m, 1H), 5.55 (q, 2H), 4.40 (dd, 2H), 2.45 (s, 3H), 1.65 (d, 3H), 1.50 (s, 3H), 1.45 (s, 3H)

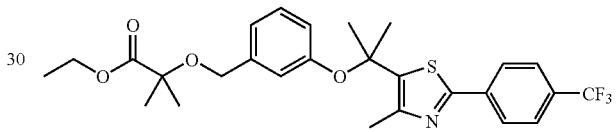

EXAMPLE 9

2-methyl-2-[3-{1-methyl-1-[4-methyl-2-(4trifluoromethylphenyl)tiazol-5-yl]ethoxy}benzyloxy]propionic acid ethyl ester TMAD (343 mg, 2.0 mmol, 1.5 equiv., Fluka) and PBu$_3$ (492 μL, 2.0 mmol, 1.5 equiv., Aldrich) in THF (50 mL) were stirred at room temperature until the solution became uncoloured. To the solution was added intermediate 19 (316 mg, 1.3 mmol, 1 equiv.) followed by intermediate 14 (400 mg, 1.3 mmol) and the reaction stirred at room temperature for 18 h. The reaction was evaporated to dryness and chromatographed eluting with CH$_2$Cl$_2$/cyclohexane (gradient 80:20 than 100:0) to afford the title compound as a clear oil (220 mg, 0.42 mmol, 32%).

MS m/z 522 (M+1) 1H NMR (CDCl$_3$): δ 7.95 (d, 2H), 7.60 (d, 2H), 7.05 (t, 1H), 6.90 (d, 1H), 6.85 (bs, 1H), 6.64 (dd, 1H), 4.30 (s, 2H), 4.10 (q, 2H), 2.50 (s, 3H), 1.75 (s, 6H), 1.35 (s, 6H), 1.18 (t, 3H)

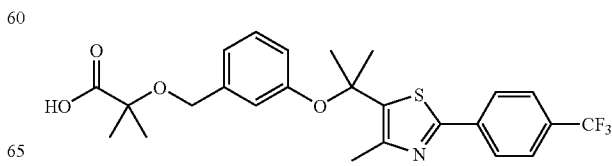

EXAMPLE 10

2-methyl-2-[3-{1-methyl-1-[4-methyl-2-(4-trifluoromethylphenyl)thiazol-5-yl]ethoxy}benzyloxy]propionic acid To example 9 (220 mg, 0.42 mmol) in EtOH (25 mL) was added 1N NaOH (843 µL, 0.84 mmol, 2 equiv.) and the reaction heated to 50° C. with stirring for 18 h. Another 3 equiv. of 1N NaOH (1.26 mL, 1.26 mmol) was added and the reaction stirred for 4 h at 50° C. The reaction was evaporated to dryness, neutralized with 1N HCl and extracted with $CH_2Cl_2$ (3×50 mL). The combined organic phase was washed with water, dried over Na2SO4, filtered and evaporated to dryness. The residue was chromatograghed eluting with $CH_2Cl_2$/MeOH (gradient: 100:0 to 95:5). The clear oil was then was titurated with pentane to afford the title compound (110 mg, 0.22 mmol, 53%) as a white solid.

MS m/z 494 (M+1); m/z 492 (M−1)

$^1$H NMR (CDCl$_3$): δ 7.90 (d, 2H), 7.60 (d, 2H), 7.05 (t, 1H), 6.90 (d, 1H), 6.80 (bs, 1H), 6.65 (dd, 1H), 4.30 (s, 2H), 2.45 (s, 3H), 1.75 (s, 6H), 1.40 (s, 6H); mp 136° C.

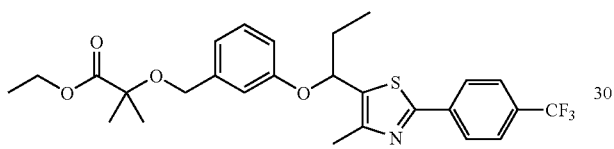

EXAMPLE 11

2-methyl-2-[3-{1-[4-methyl-2-(4-trifluoromethylphenyl)tiazol-5-yl]propyloxy}benzyloxy]propionic acid ethyl ester The TMAD (377 mg, 2.2 mmol, 1.5 equiv., Fluka) and PBu$_3$ (540 µL, 2.2 mmol, 1.5 equiv., Aldrich) in THF (50 mL) were stirred at room temperature until the solution became uncolored. To the solution was added intermediate 19 (383 mg, 1.6 mmol, 1.1 equiv.) followed by intermediate 13 (440 mg, 1.5 mmol) and the reaction stirred at room temperature for 18 h. The reaction was evaporated to dryness and chromatographed eluting with cyclohexane/EtOAc (gradient: 95:5 to 8:2) to afford the title compound as a clear oil (220 mg, 0.42 mmol, 29%).

MS m/z 522 (M+1)

$^1$H NMR (CDCl$_3$): δ 8.00 (d, 2H), 7.65 (d, 2H), 7.15 (t, 1H), 6.95 (bs, 1H), 6.90 (d, 1H), 6.75 (m, 1H), 5.35 (t, 1H), 4.40 (s, 2H), 4.20 (q, 2H), 2.50 (s, 3H), 2.15 (m, 1H), 1.95 (m, 1H), 1.46 (s, 3H), 1.44 (s, 3H), 1.25 (t, 3H), 1.02 (t, 3H)

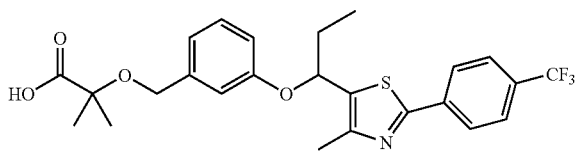

EXAMPLE 12

2-methyl-2-[3-{1-[4-methyl-2-(4-trifluoromethylphenyl)thiazol-5-yl]propyloxy}benzyloxy]propionic acid To example 11 (220 mg, 0.42 mmol) in EtOH (25 mL) was added 1N NaOH (844 µL, 0.84 mmol, 2 equiv.) and the reaction heated to 60° C. with stirring for 3 h. The reaction was evaporated to dryness, treated with 1N HCl and extracted with $CH_2Cl_2$ (3×50 mL). The combined organic phase was washed with water, dried over Na$_2$SO$_4$, filtered and evaporated to dryness. The residue was chromatograghed eluting with $CH_2Cl_2$ (100%) and then $CH_2Cl_2$/MeOH (95:5) to afford the title compound (40 mg, 0.08 mmol, 19%) as a clear oil.

MS m/z 492 (M−1)

$^1$H NMR (CDCl$_3$): δ 7.80 (d, 2H), 7.50 (d, 2H), 7.10 (t, 1H), 6.90 (bs, 1H), 6.80 (d, 1H), 6.70 (m, 1H), 5.25 (t, 1H), 4.35 (s, 2H), 2.40 (s, 3H), 2.05 (m, 1H), 1.85 (m, 1H), 1.40 (s, 3H), 1.38 (s, 3H), 1.10 (t, 3H)

The following intermediates and ligands were prepared for the transfection assay described below:

(i) 2-{2-methyl-4-[({4-methyl-2-[4-(trifluoromethyl)phenyl]-1,3-thiazol-5-yl}-methyl)sulfanyl]phenoxy}acetic acid This compound was used as a PPARdelta reference in the transfection assays described below and was prepared according to the following method:

Intermediate A:

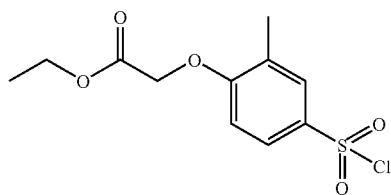

Chlorosulfonic acid (15 mL) was cooled to 0° C. then 10.0 g (0.05M) of ethyl (2-methylphenoxyacetate) was added over 10 min. The reaction mixture was stirred at 0–5° C. for 30 m, the bath was removed and stirring continued for 2 h. The reaction mixture was poured into ice, forming a white solid which was washed with ice water and dried under high vacuum affording the title compound (12.846 g ,86%).

Intermediate B:

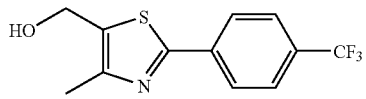

To a well stirred solution of LiAlH$_4$ (1.52 g, 40 mmol) in dry THF (50 mL) at 0° C., was slowly added a solution of ethyl 4-methyl-2-[4-(trifluoromethyl)phenyl]-thiazole-5-carboxylate (12.6 g, 40 mmol) in dry THF (50 mL). The mixture was stirred at room temperature for 2 hs. The reaction was quenched by slow addition at 0° C. of water (2 mL), 5N NaOH (2 mL) and water (6 mL). The precipitate was filtered, washed with EtOAc, MeOH, CH₂Cl₂ and THF. After evaporation, a yellow solid was obtained, that was crystallyzed from MeOH-water to afford intermediate B depicted above (9.90 g, 36 mmol, 90%) as a yellow solid mp 120–122 ° C.

Intermediate C:

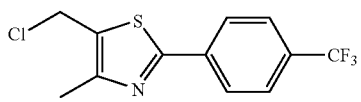

To a cold (0° C.) stirred solution of intermediate B (8.2 g, 30 mmol) and Et₃N (6.07 g, 8.36 mL, 60 mmol), in dry CH₂Cl₂ (120 mL) was slowly added MeSO₂Cl (5.49 g, 3.71 mL, 48 mmol). After 2 hs at 0° C. more Et₃N (6 mmol) and MeSO₂Cl (4.8 mmol) were added. After 2 more h a tlc (hexane:EtOAc, 1:1) showed complete reaction. The reaction mixture was diluted with CH₂Cl₂ (120 mL) and washed with NaHCO₃ (sat.) (2×240 mL) and water (2×240 mL), dried, filtered and evaporated to afford intermediate C (8.0 g, 27 mmol, 90%) as a yellow solid.

2-{2-methyl-4-[({4-methyl-2-[4-(trifluoromethyl) phenyl]-1,3-thiazol-5-yl}methyl)sulfanyl] phenoxy}acetic acid

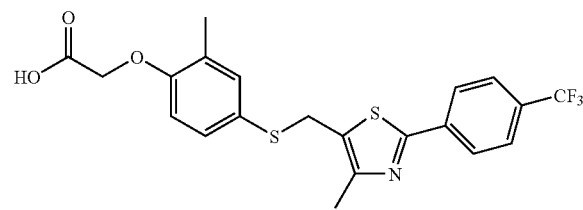

Intermediate A (4.68 g, 16 mM) was refluxed with 9.6 g of tin powder in ethanol (20 mL) and dioxane/HCl (20 mL). After 3 h the reaction mixture was poured into ice and CH₂Cl₂ (200 mL) and filtered. The phases were separated and the aqueous layer was extracted 2×50 mL CH₂Cl₂. The combined organic layers were dried (MgSO₄), filtered and evaporated to yield 3.5 g (97%). This material readily forms disulfides and therefore was used immediately. It was dissolved in acetonitrile (50 mL) with intermediate C (4.0 g, 14.0 mM) and Cs₂CO₃ (10.1 g, 31.0 mM) and stirred for 1 h then diluted with ether (200 mL) and water (200 mL). The phases were separated and the organic phase was washed 2× NaOH 0.1N (50 mL), dried (MgSO₄), filtered and evaporated to afford crude product (6.57 g,) which was slurried in hexane:ether (1:1) and filtered to yield pure intermediate D (5.0 g, 74%). This material was hydrolyzed as described below to prepare the title compound. A solution of the corresponding ester (Intermediate D) (1 mmol) in THF (10 mL) (in some cases few drops of MeOH were added to help solubility), was treated with 1N LiOH in water (2 mL, 2 mmol), and stirred 16 h at room temperature (when reactions were slow, the temperature was elevated to 50° C.). The solution was neutralized with 1N HCl (2 mL, 2 mmol) and the organic solvent evaporated to afford an aqueous solution with an insoluble product. If the insoluble was a solid, it was filtered and dried to afford the final product. If the insoluble was an oil, it was extracted with EtOAc (30 mL). The organic solution was separated, washed with water (2×30 mL), dried, filtered, and evaporated to afford the final product.

(ii) 2-methyl-2-[4-{[(4-methyl-2-[4-trifluoromethylphenyl]-thiazol-5-yl carbonyl)amino]methyl}-phenoxy]propionic acid This compound was used as a PPAR alpha reference in the transfection assay described below and was prepared according to the following method.

Intermediate E:

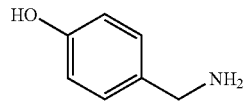

Same procedure as Stout, D. M. *J. Med. Chem.* 1983, 26(6), 808–13. To 4-methoxybenzyl amine (25 g, 0.18 mol; Aldrich) was added 46% HBr in H₂O (106 ml, 0.9 mol; Aldrich). The reaction was refluxed overnight, then the reaction cooled to 0° C. and neutralized to pH7 slowly with KOH₍ₛ₎. The reaction is allowed to stir for ~30 min, then the solid filtered and dried. The solid redisolved in hot MeOH, filtered and the solution cooled to afford 19 g (85%) intermediate E. ¹H NMR (DMSO-d₆): δ 8.0 (bs, 1H), 7.2 (d, 2H), 6.75 (d, 2H), 3.85 (s, 2H), 3.50 (bs, 2H).

Intermediate F:

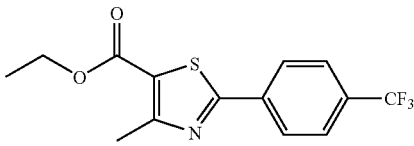

A solution of ethyl 2-chloroacetoacetate (35.3 g, 29.7 mL, 0.21 mol) and 4-(trifluoromethyl)thiobenzamide (44 g, 0.21 mol) in EtOH (300 mL) was refluxed overnight. After cooling to room temperature the solvent removed in vacuo. The final product (intermediate F) was recrystallized from a minimum of MeOH to afford 40 g (59%) of final product as a white solid. ¹H NMR (CDCl₃): δ 8.10 (d, 2H), 7.70 (d, 2H), 4.40 (q, 2H), 2.80 (s, 3H), 1.4 (t, 3H).

Intermediate G:

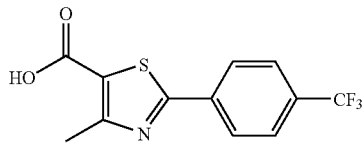

To intermediate F (1.84 g, 5.8 mmol) in THF was added 1N LiOH (6 mL, 6 mmol) and the reaction stirred at room temperature. After ~3 h, the reaction neutralized with 1N HCl, extracted 3×100 mL EtOAc, dried over Na₂SO₄, filtered and the solvent removed under vaccum to afford 1.5 g (89%) intermediate G as a white solid. ¹H NMR (DMSO-d₆): δ 13.55 (bs, 1H), 8.25 (d, 2H), 7.95 (d, 2H), 2.75 (s, 3H).

Intermediate H:

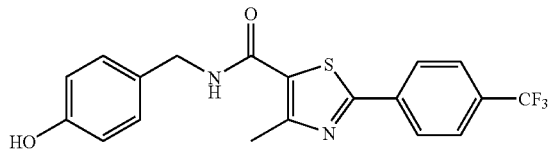

To intermediate G (1 g, 7 mmol) in CH₂Cl₂/DMF (1:1) was added HOBT (565 mg, 4.2 mmol; Aldrich), EDC (800 mg, 4.2 mmol; Aldrich) and intermediate E (860 mg, 7 mmol). The reaction stirred at room temperature for 18 h. The solvent removed in vacuo, treated with H₂O and extracted 3×100 mL CH₂Cl₂. The organic phases combined and washed with 1N HCl, dried over Na₂SO₄, filtered and evaporated to afford a mixture (N-substituted and N,O-substituted). The mixture disolved in MeOH and treated with 1N NaOH. The reaction stirred 18 h at 50° C. The solvent removed in vacuo, dissolved in CH₂Cl₂, washed with H₂O, and dried over Na₂SO₄. The solvent evaporated the residue chromatographed (CH₂Cl₂/MeOH: 99/1) to afford 610 mg (47%) of intermediate H as a white solid.

¹H NMR (DMSO-d₆): δ 9.30 (s, 1H), 8.80 (t, 1H), 8.20 (d, 2H), 6.70 (d, 2H), 4.35 (d, 2H), 2.6 (s, 3H).

Intermediate I:

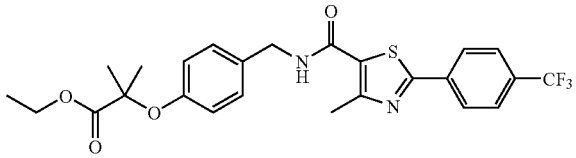

2-methyl-2-[4-{[(4-methyl-2-[4-trifluoromethylphenyl]thiazol-5-ylcarbonyl)amino]methyl}phenoxy] propionic acid ethyl ester To intermediate H (710 mg, 1.81 mmol) in DMF (50 mL) was added the K₂CO₃ (275 mg, 1.99 mmol) followed by the ethyl 2-bromo-2-methylpropanate (280 μL, 1.91 mmol; Aldrich) and the reaction heated to 80° C. After 18 h, the reaction cooled to room temperature and the solvent removed in vacuo. The residue treated with water (200 mL), extracted 3×50 mL CH₂Cl₂, dried over Na₂SO₄, filtered and the solvent removed under vaccum. The residue was chromatographed (CH₂Cl₂/MeOH: 99/1). To afford 680 mg (77%) of Intermediate I as a clear oil. ¹H NMR(CDCl₃): δ 7.95 (d, 2H), 7.60 (d, 2H), 7.15 (d, 2H), 6.75 (d, 2H), 6.05 (t, 1H), 4.45 (d, 2H), 4.15 (q, 2H), 2.65 (s, 3H), 1.50 (s, 6H), 1.20 (t, 3H).

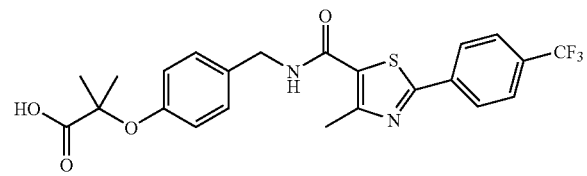

2-methyl-2-[4-{[(4-methyl-2-[4-trifluoromethylphenyl]-thiazol-5-ylcarbonyl)amino]methyl}phenoxy] propionic acid To Intermediate I (680 mg, 1.39 mmol) in MeOH was added 1N NaOH (1.6 mL, 1.6 mmol) and the reaction stirred at 60° C. After 18 h, the reaction cooled to room temperature and the solvent evaporated. The residue treated with 1N HCl, extracted 3×20 mL THF and the solvent removed under vacuum. 500 mg (75%) The title compound was precipitated as a white solid from a minimum CH₂Cl₂ and pentane. mp: changes the form between 60–70° C.; LC/MS (m/z): 477.22 (100%, AP−), 479.12 (100%, AP+); anal. C₂₃H₂₁F₃N₂O₄S: C, 5.71; (57.73), H, 4.56; (4.42), N, 5.77; (5.85), S, 6.15; (6.70).

Binding Assay:

Compounds were tested for their ability to bind to hPPAR gamma hPPARalpha or PPARdelta using a Scintillation Proximity Assay (SPA). The PPAR ligand binding domain (LBD) was expressed in *E. coli* as polyHis tagged fusion proteins and purified. The LBD was then labeled with biotin and immobilized on streptavidin-modified scintillation proximity beads. The beads were then incubated with a constant amount of the appropriate radioligand (³H-BRL 49653 for PPARgamma, radiolabelled 2-(4-(2-(2,3-Ditritio-1-heptyl-3-(2,4-difluorophenyl)ureido)ethyl)phenoxy)-2-methylbutanoic acid for hPPAR alpha (see WO 00/08002)and labelled GW 2433 (see Brown, P. J et al. *Chem. Biol.* 1997, 4, 909–918 for the structure and synthesis of this ligand) for PPAR delta) and variable concentrations of test compound, and after equilibration the radioactivity bound to the beads was measured by a scintillation counter. The amount of nonspecific binding, as assessed by control wells containing 50 μM of the corresponding unlabeled ligand, was subtracted from each data point. For each compound tested, plots of ligand concentration vs. CPM of radioligand bound were constructed and apparent $K_I$ values were estimated from nonlinear least squares fit of the data assuming simple competitive binding. The details of this assay have been reported elsewhere (see, Blanchard, S. G. et. al. *Development of a Scintillation Proximity Assay for Peroxisome Proliferator-Activated Receptor gamma Ligand Binding Domain. Anal. Biochem.* 1998, 257, 112–119).

Transfection Assay:

Compounds were screened for functional potency in transient transfection assays in CV-1 cells for their ability to activate the PPAR subtypes (transactivation assay). A previously established chimeric receptor system was utilized to allow comparison of the relative transcriptional activity of the receptor subtypes on the same target gene and to prevent endogenous receptor activation from complicating the interpretation of results. See, for example, Lehmann, J. M.; Moore, L. B.; Smith-Oliver, T. A.; Wilkison, W. O.; Willson, T. M.; Kliewer, S. A., *An antidiabetic thiazolidinedione is a high affinity ligand for peroxisome proliferator-activated receptor γ (PPARγ), J. Biol. Chem.,* 1995, 270, 12953–6. The ligand binding domains for murine and human PPAR alpha, PPAR gamma, and PPAR delta were each fused to the yeast transcription factor GAL4 DNA binding domain. CV-1 cells were transiently transfected with expression vectors for the respective PPAR chimera along with a reporter construct containing five copies of the GAL4 DNA binding site driving expression of secreted placental alkaline phosphatase (SPAP) and β-galactosidase. After 16 h, the medium was exchanged to DME medium supplemented with 10% delipidated fetal calf serum and the test compound at the appropriate concentration. After an additional 24 h, cell extracts were prepared and assayed for alkaline phosphatase and β-galactosidase activity. Alkaline phosphatase activity was corrected for transfection efficiency using the β-galactosidase activity as an internal standard (see, for example, Kliewer, S. A., et. al. *Cell* 83, 813–819 (1995)). Rosiglitazone (BRL 49653) was used as a positive control in the hPPAR gamma assay. The positive control in the hPPAR alpha assays was 2-methyl-2-[4-{[(4-methyl-2-[4-trifluoromethylphenyl]-thiazol-5-yl-carbonyl)amino]methyl}-phenoxy]propionic acid (described above and in WO 01/40207). The positive control for PPAR delta assays was 2-{2-methyl-4-[({4-methyl-2-{trifluoromethyl)phenyl]-1,3-thiazol-5-yl}methyl)sulfanyl]phenoxy}acetic acid (described above and also in WO 01/00603).

What is claimed is:

1. A compound of formula (I) and pharmaceutically acceptable salts, solvates and hydrolysable esters thereof

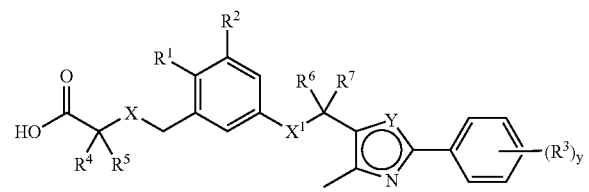

wherein
X is O or S;
$X^1$ is O or S;
Y is S or O;
$R^1$ and $R^2$ are independently H, methyl, or halogen;
$R^4$ and $R^5$ are independently H or $C_{1-3}$ alkyl or $R^4$ and $R^5$ may, together with the carbon atom to which they are bonded, form a 3–5 membered cycloalkyl ring;
$R^6$ and $R^7$ are independently H, $C_{1-3}$ alkyl, or allyl;
each $R^3$ is independently halogen, $C_{1-6}$ straight or branched alkyl, or $CF_3$; and y is 0, 1, 2, 3, 4, or 5.

2. A compound according to claim 1 wherein X is O.
3. A compound according to claim 1 wherein $X^1$ is O.
4. A compound according to claim 1 wherein at least one of $R^1$ and $R^2$ is H.
5. A compound according to claim 4 wherein $R^1$ and $R^2$ are both H.
6. A compound according to claim 1 wherein $R^6$ and $R^7$ are both H.
7. A compound according to claim 1 wherein Y represents S.
8. A compound according to claim 1 wherein $R^4$ and $R^5$ are both H or $R^4$ and $R^5$ are both $CH_3$.
9. A compound according to claim 8 wherein $R^4$ and $R^5$ are both $CH_3$.

10. A compound according to claim 1 wherein y represents 1 or 2.
11. A compound according to claim 10 wherein y represents 2.
12. A compound according to claim 11 wherein one of $R^3$ substituents is halogen.
13. A compound according to claim 12 wherein one of the $R^3$ substituents is halogen and the other is $CF_3$.
14. A compound according to claim 10 wherein y represents 1.
15. A compound according to claim 14 wherein the $R^3$ substituent is in the para position.
16. A compound according to claim 15 wherein $R^3$ is $CF_3$.
17. A compound of formula (I) selected from:
2-methyl-2-{(3-[4-methyl-2-(4-trifluoromethylphenyl) thiazol-5-yl]methoxy)benzyloxy}propionic acid ethyl ester;
2-methyl-2-{(3-[4-methyl-2-(4-trifluoromethylphenyl) thiazol-5-yl]methoxy)benzyloxy}propionic acid;
2-{[(3-[4-methyl-2-(4-trifluoromethylphenyl)thiazol-5-yl]methoxy)benzyl]thio}acetic acid methyl ester;
2-{[(3-[4-methyl-2-(4-trifluoromethylphenyl)thiazol-5-yl]methoxy)benzyl]thio}acetic acid;
2-{(3-[4-methyl-2-(4-trifluoromethylphenyl)thiazol-5-yl]methoxy)benzyloxy}acetic acid ethyl ester;
2-{(3-[4-methyl-2-(4-trifluoromethylphenyl)thiazol-5-yl]methoxy)benzyloxy}acetic acid;
2-methyl-2-[3-{1-[4-methyl-2-(4-trifluoromethylphenyl)thiazol-5-yl]ethoxy}benzyloxy]propionic acid ethyl ester;
2-methyl-2-[3-{1-[4-methyl-2-(4-trifluoromethylphenyl)thiazol-5-yl]ethoxy}benzyloxy]propionic acid;
2-methyl-2-[3-{1-methyl-1-[4-methyl-2-(4-trifluoromethylphenyl)thiazol-5-yl]ethoxy}benzyloxy]propionic acid ethyl ester;
2-methyl-2-[3-{1-methyl-1-[4-methyl-2-(4-trifluoromethylphenyl)thiazol-5-yl]ethoxy}benzyloxy]propionic acid;
2-methyl-2-[3-{1-[4-methyl-2-(4-trifluoromethylphenyl)thiazol-5-yl]propyloxy}benzyloxy]propionic acid ethyl ester;
2-methyl-2-[3-{1-[4-methyl-2-(4-trif luoromethylphenyl)thiazol-5-yl]propyloxy}benzyloxy]propionic acid; and
pharmaceutically acceptable salts, solvates and hydrolysable esters thereof.

18. A pharmaceutical composition comprising a compound according to claim 1.
19. A pharmaceutical composition according to claim 18 further comprising a pharmaceutically acceptable diluent or carrier.

* * * * *